(12) United States Patent
Howerton, Jr.

(10) Patent No.: US 7,756,326 B2
(45) Date of Patent: Jul. 13, 2010

(54) METHOD FOR FORMING AND DISTRIBUTING A COMPOSITE FILE INCLUDING A DENTAL IMAGE AND ASSOCIATED DIAGNOSIS

(76) Inventor: William Bruce Howerton, Jr., 224 Edgewater Cir., Chapel Hill, NC (US) 27516

( * ) Notice: Subject to any disclaimer, the term of this patent is extended or adjusted under 35 U.S.C. 154(b) by 1001 days.

(21) Appl. No.: 11/465,044

(22) Filed: Aug. 16, 2006

(65) Prior Publication Data
US 2007/0258638 A1 Nov. 8, 2007

Related U.S. Application Data

(63) Continuation-in-part of application No. 11/417,381, filed on May 4, 2006.

(51) Int. Cl.
*G06K 9/00* (2006.01)
(52) U.S. Cl. .................... 382/154; 382/128; 433/24
(58) Field of Classification Search ............ 382/154, 382/155, 156; 433/24
See application file for complete search history.

(56) References Cited

U.S. PATENT DOCUMENTS

| | | | |
|---|---|---|---|
| 5,497,776 A | 3/1996 | Yamazaki et al. | |
| 5,715,823 A * | 2/1998 | Wood et al. | 600/437 |
| 6,041,143 A * | 3/2000 | Chui et al. | 382/232 |
| 6,621,918 B1 | 9/2003 | Hu et al. | |
| 7,165,718 B2 | 1/2007 | Blancas et al. | |
| 7,234,937 B2 * | 6/2007 | Sachdeva et al. | 433/24 |
| 2004/0197727 A1 | 10/2004 | Sachdeva et al. | |
| 2005/0271996 A1 | 12/2005 | Sporbert et al. | |

* cited by examiner

*Primary Examiner*—Samir A Ahmed
*Assistant Examiner*—Ruiping Li
(74) *Attorney, Agent, or Firm*—Womble Carlyle Sandridge & Rice, PLLC

(57) ABSTRACT

A method of providing dental-related imaging data of a patient to a dental practitioner is provided, the dental-related imaging data being obtained by a third party imaging provider at a third-party imaging provider site using a three-dimensional digital imaging device. Three-dimensional image data of the maxillofacial complex of the patient is obtained with the imaging device and analyzed to form a diagnosis. A two-dimensional image associated with the diagnosis is formed from the three-dimensional image data, and the two-dimensional image and diagnosis are combined into a composite file as part of the dental-related imaging data. The dental-related imaging data is stored in encrypted read-only format executable by a standard multi-media player and made available to the dental provider in a secure arrangement. The composite file is thereby selectively viewable by the dental provider for determining an appropriate treatment for the patient. Associated methods and apparatuses are also provided.

6 Claims, 7 Drawing Sheets

METHOD FOR FORMING AND DISTRIBUTING A COMPOSITE FILE INCLUDING A DENTAL IMAGE AND ASSOCIATED DIAGNOSIS

CROSS-REFERENCE TO RELATED APPLICATION

This application is a Continuation-in-Part of U.S. Utility application Ser. No. 11/417,381, filed May 4, 2006, which is incorporated by reference herein in its entirety.

BACKGROUND OF THE INVENTION

1. Field of the Invention

The present invention relates to diagnostic imaging systems and, more particularly, to a method and apparatus for forming and distributing a composite file including a dental image and associated diagnosis.

2. Description of Related Art

Radiographic imaging in dentistry has historically been most commonly associated with two-dimensional images. That is, any dental-related radiographic imaging likely produces a two-dimensional representation of the imaged area that includes distortion resulting from the attempt to image a three-dimensional subject. Developments in three-dimensional imaging such as, for example, conebeam technology, has allowed three-dimensional imaging to be offered to private practitioners, such as dentists. Because the three-dimensional subject (patient) can now be imaged with a three-dimensional imaging technique, more information, as well as more accurate information, can be provided to the practitioner (also referred to herein as a "referring dentist") to allow for more precise and successful treatment of the patient. Along with this improvement in finding and treating such problems comes an increase in patient satisfaction. However, since many dental practitioners are accustomed to viewing and performing a diagnosis through two-dimensional imaging of a three-dimensional subject, many such practitioners may be unable to perform a diagnosis or otherwise make efficient use of the wealth of information provided by images produced by three-dimensional imaging techniques.

In addition, though a significant amount of two-dimensional radiographic images in the field of dentistry are provided in a film format, an increasing number of private practitioners are turning to digital imaging as an alternative. Such digital imaging, for example, eliminates the use of film and developing solutions. Furthermore, the resultant radiographic images are in electronic form, can be stored in computers, can be transmitted over the Web, and/or transferred onto portable hard media, such as a compact disc (CD). In some instances, radiographic imaging devices implementing digital imaging techniques may also require less radiation per exposure.

In order for three-dimensional imaging of the oral and maxillofacial complex to be accomplished using conebeam technology, data is collected while exposing the entire maxillofacial complex to the three-dimensional imager over a full 360°. The raw data collected via the imager can be reconstructed, for example, into 512 axial images and stored in a DICOM format. The Digital Imaging and Communications in Medicine (DICOM) standard was created by the National Electrical Manufacturers Association (NEMA) to aid the distribution and viewing of medical images, such as CT scans, MRIs, and ultrasound. Part 10 of the standard describes a file format for the distribution of images. Most refer to image files which are compliant with Part 10 of the DICOM standard as DICOM format files.

A single DICOM file contains both a header (which stores information about the patient's name, the type of scan, image dimensions, etc), as well as all of the image data (which can contain information in three dimensions). The DICOM image data can be compressed (encapsulated) to reduce the image size, and files can be compressed using lossy or lossless variants of the JPEG format, as well as a lossless Run-Length Encoding format (which is identical to the packed-bits compression found in some TIFF format images). In this regard, DICOM is among the most common standards for receiving scans from a hospital.

The software included with the radiographic (conebeam) imaging machine is typically configured to reconstruct the collected data to produce images in any plane and/or three-dimensional volume renderings of the maxillofacial complex. Once a planar image or volume rendering is produced, the image can be saved at the imaging site as a bitmap or JPEG image. In addition to images, video clips can sometimes be created and saved as AVI files. At this point, bitmap or JPEG images of the patient's region of interest must be somehow delivered to the referring dentist, along with a description of the images, and possibly including an interpretation of findings. However, any accompanying description or interpretation of the image data must often be prepared separately from the image data and stored as a separate file.

Two forms of delivery of the patient image data to the referring dentist are common. One form is printing the appropriate images on film using a high-resolution printer and including a separate document containing a description of the images and an interpretation of the findings of the imaging specialist. However, such a method typically implements costly high-resolution printing on expensive film media. Further, it may be difficult to correlate the images with a separate printed text (interpretations), delivery of this information through mail or other delivery channels is slow, and correcting images or typographical errors in the text often requires appropriately amended film or documentation to be prepared by the imaging provider and then re-forwarded to the referring dentist.

The second form of delivery is providing the referring dentist with the entire DICOM data set on a CD or other portable media, along with an appropriate DICOM viewer. In practice, a DICOM viewer is particularly configured for a specified application. As such, the common thread between various DICOM viewers is generally limited to the capability of opening a DICOM format file. Further, the entire DICOM data set is often very large in size. In addition, even though any two or three-dimensional images, or video clip, selected from the DICOM data set may be included with the DICOM data set on the CD, any accompanying description or interpretation of findings must still be provided separately from the images. Dentists, however, often do not have the time or skill to manipulate such large DICOM data sets and, since this method involves delivery to the referring dentist on hard media, such DICOM viewers and data may not be well-received by the referring dentist due to the time for delivery and/or the cumbersome and extensive nature of the provided data.

Another possible shortcoming in delivering to the referring dentist images produced from three-dimensional volume data sets is that the final radiographic study cannot be easily shared with more than one dentist that may be involved in treating the same patient. That is, sharing such images between dentists, who may be remotely located, may be difficult and/or cumbersome, particularly where concurrent viewing of a particular image may be required for conferring between the remotely located dentists. This is due, at least in part, to the size and complexity of the DICOM data set, the specialized nature of the DICOM viewer, and the separate file(s) for the accompanying description and/or interpretation of findings.

Thus, there exists a need for a more efficient method of forming and distributing composite image data, including a dental image and associated diagnosis, that allows the referring dentist(s) more flexibility in receiving and viewing the images of the patient and then formulating an appropriate treatment as a result thereof.

BRIEF SUMMARY OF THE INVENTION

The above and other needs are met by the present invention which, in one aspect comprises a method of providing dental-related imaging data of a patient to a dental practitioner. The dental-related imaging data is obtained by a third party imaging provider at a third-party imaging provider site using a three-dimensional digital imaging device. Three-dimensional image data of at least a portion of a maxillofacial complex of the patient is obtained with the imaging device, and then analyzed to form a diagnosis. A two-dimensional image associated with the diagnosis is then formed from the three-dimensional image data, and combined with the diagnosis into a composite file as part of the dental-related imaging data of the patient. The dental-related imaging data is stored at the third-party imaging provider site in a read-only format executable by a commercially-available multi-media player. The dental-related imaging data in encrypted read-only format is made available to the dental provider in a secure arrangement, such that the composite file is selectively viewable by the dental provider via the multi-media player so as to allow the dental provider to determine an appropriate treatment for the patient. The dental-related imaging data can be made available to the dental provider, for example, by publishing the dental-related imaging data on the Internet in an encrypted secure read-only format selectively executable on-line by the dental provider with the standard commercially-available multi-media player. Alternatively, the dental-related imaging data can be made available to the dental provider, for example, by saving the dental-related imaging data in an encrypted secure read-only format on a portable media element and then delivering the portable media element to the dental provider for selective execution of the dental-related imaging data by the dental provider on a local dental provider computer device with the standard commercially-available multi-media player.

Accordingly, embodiments of the present invention provide distinct advantages as further discussed herein.

BRIEF DESCRIPTION OF THE DRAWINGS

Figure 1:
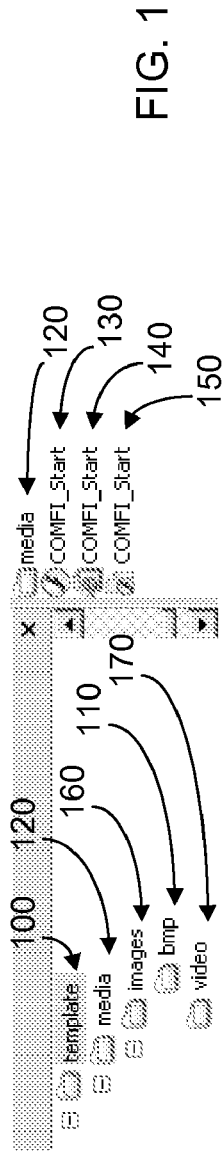
Figure 2:
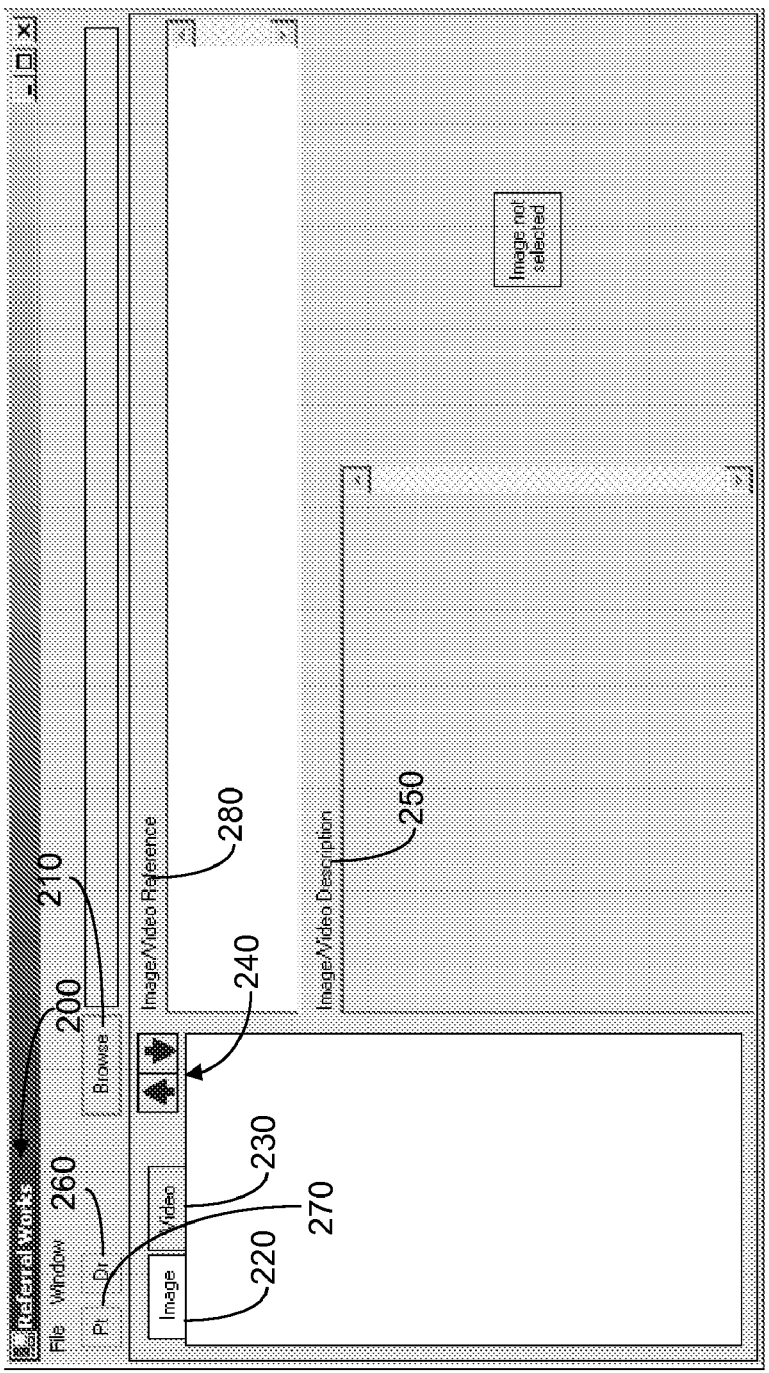
Figure 3:
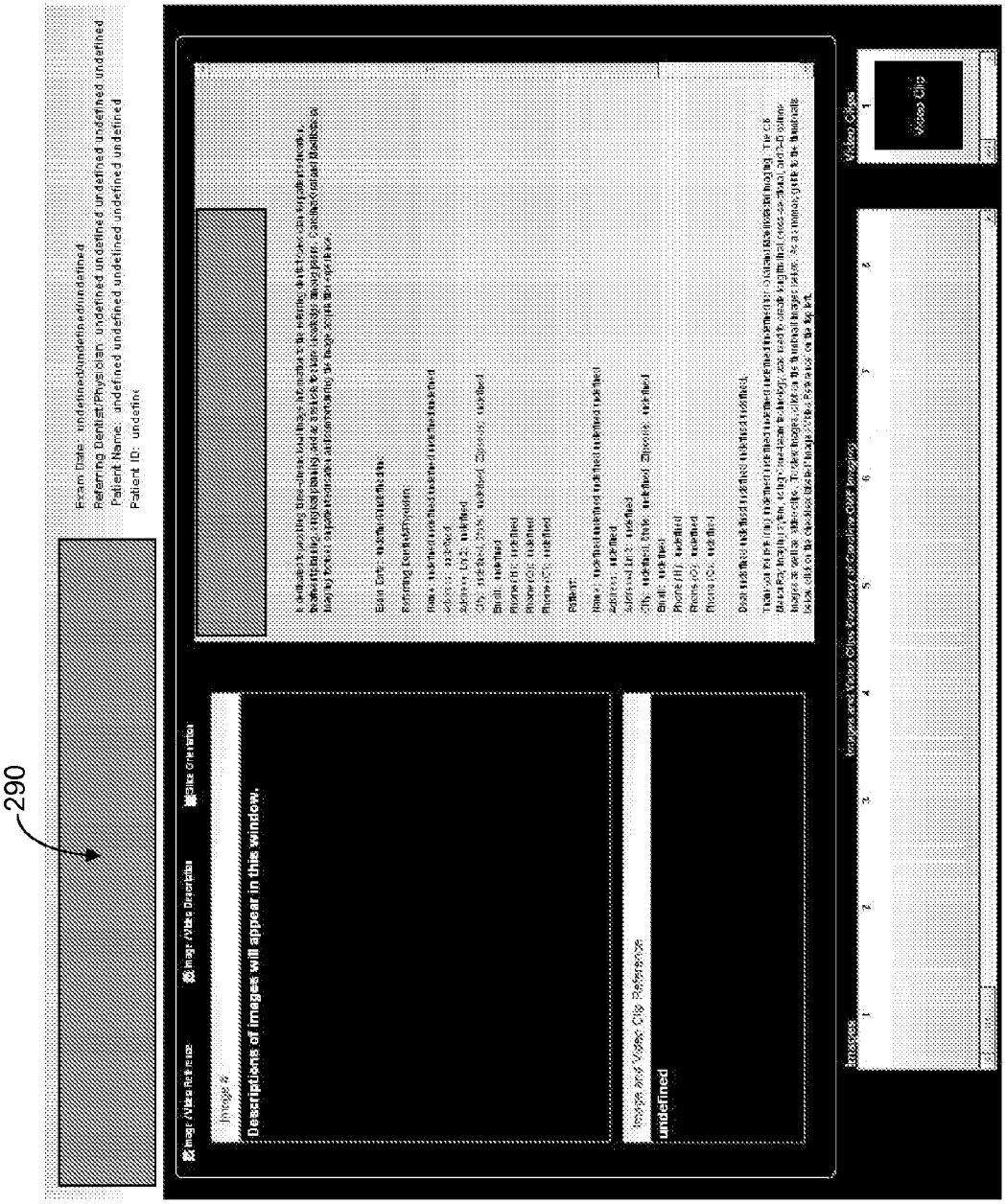
Figure 4:
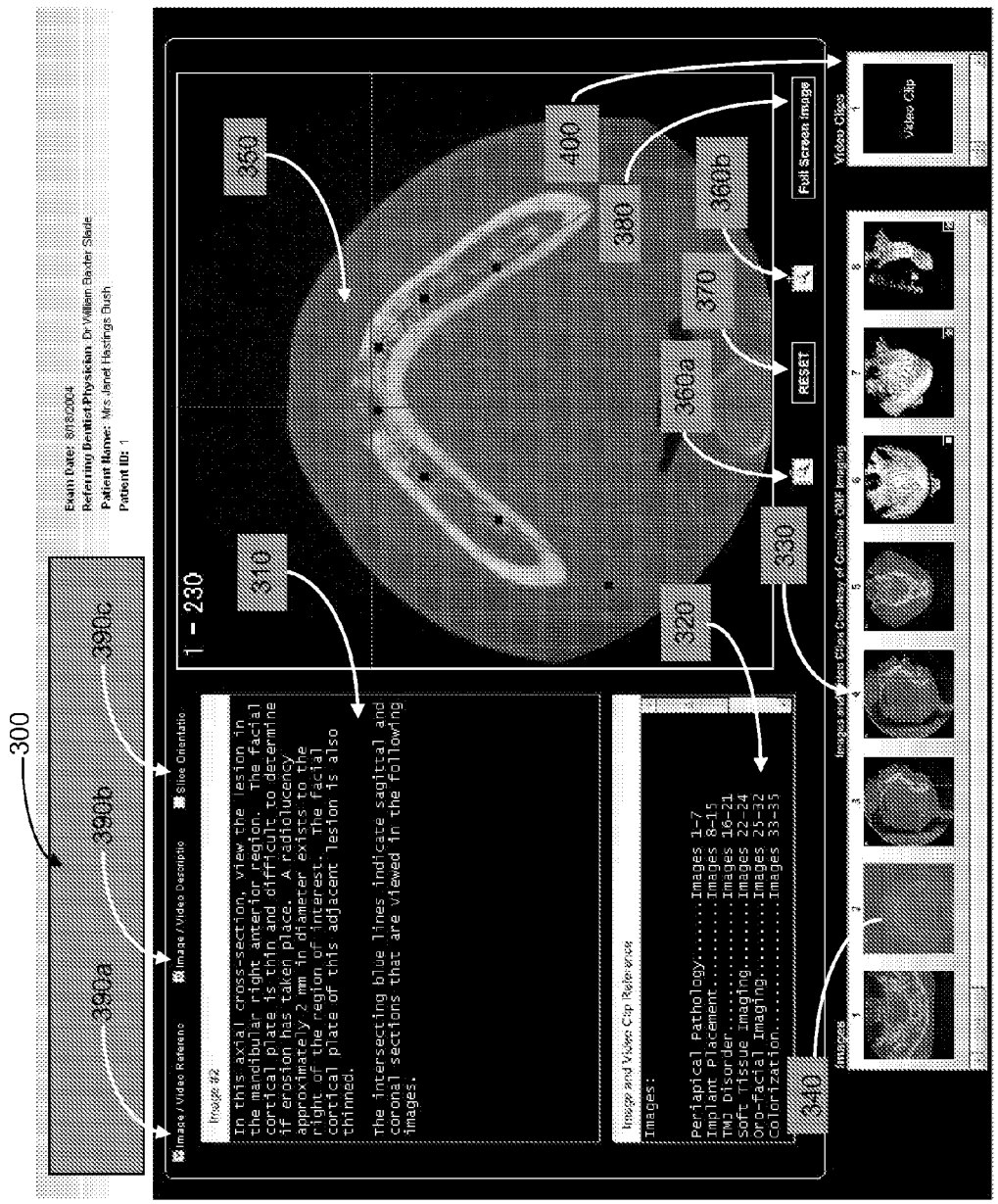
Figure 5:
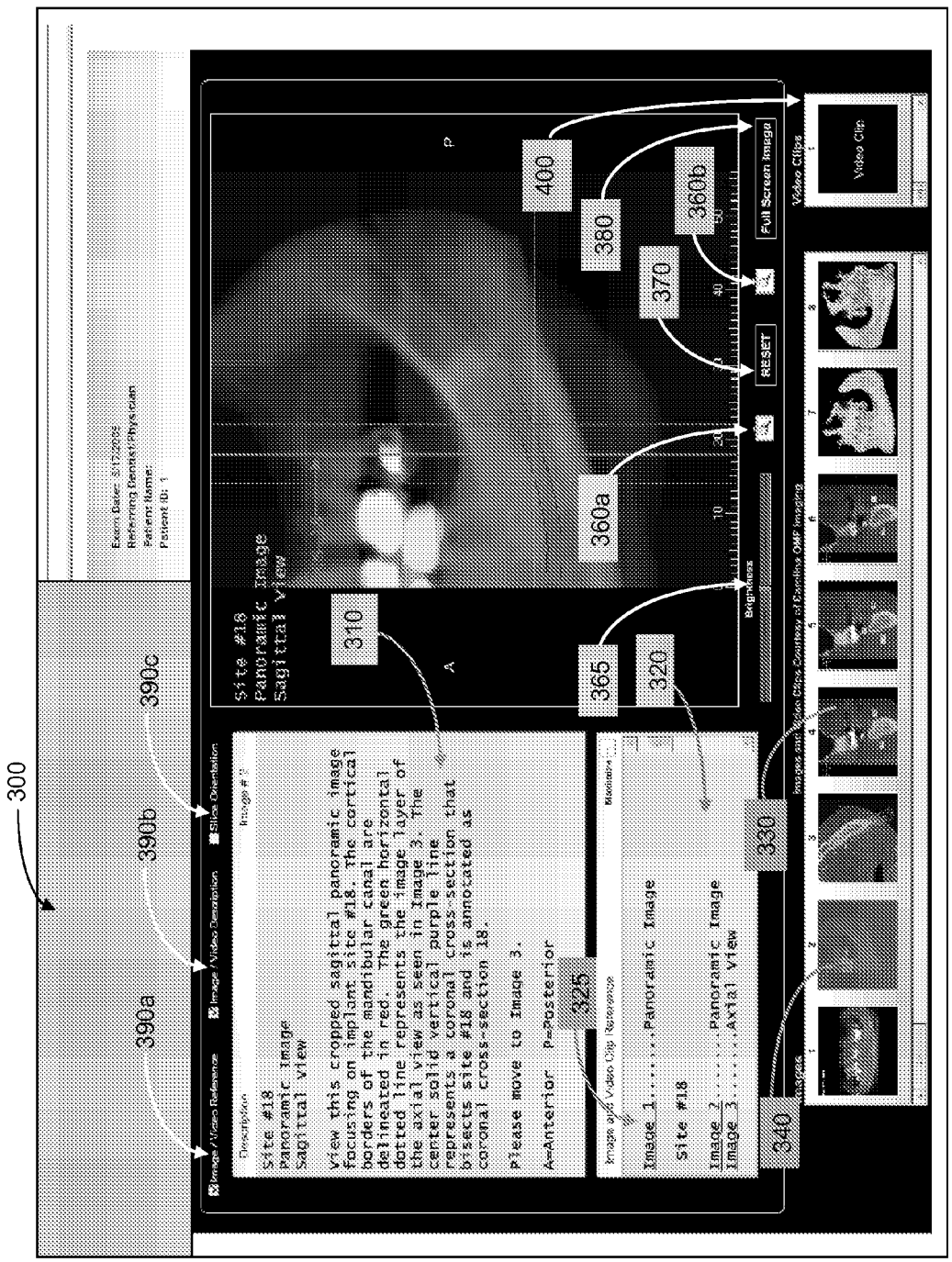
Figure 6:
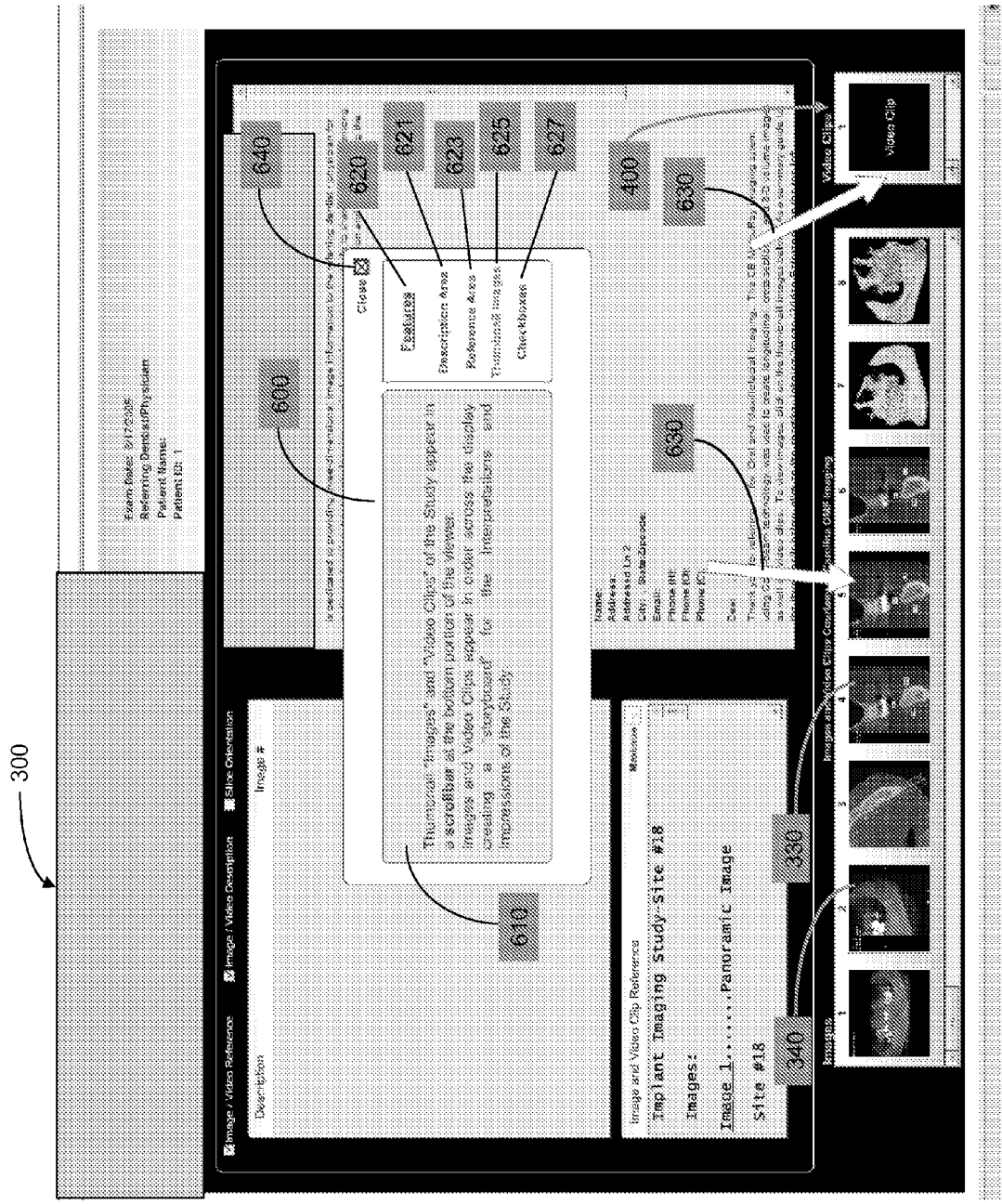
Figure 7:
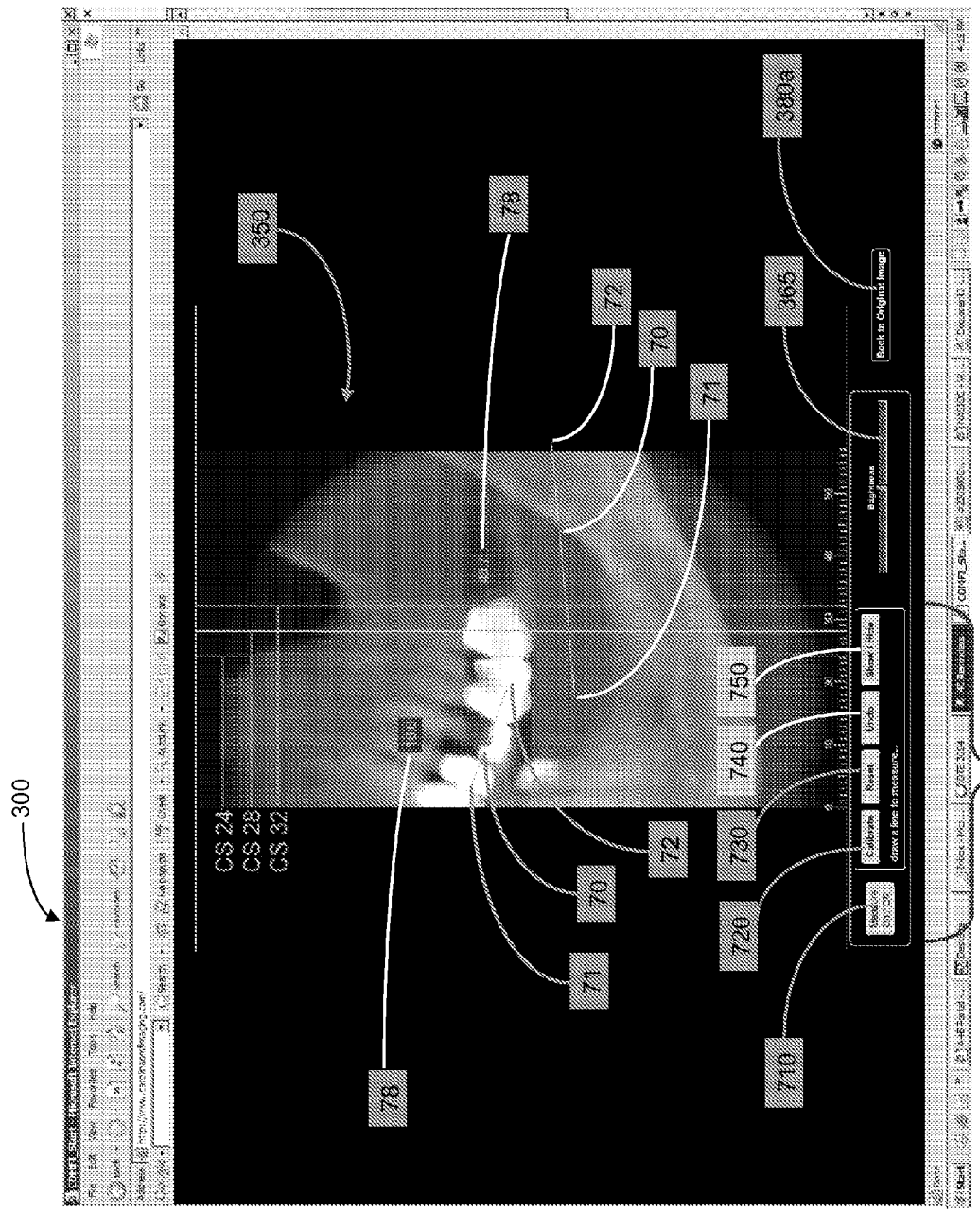
Figure 8:
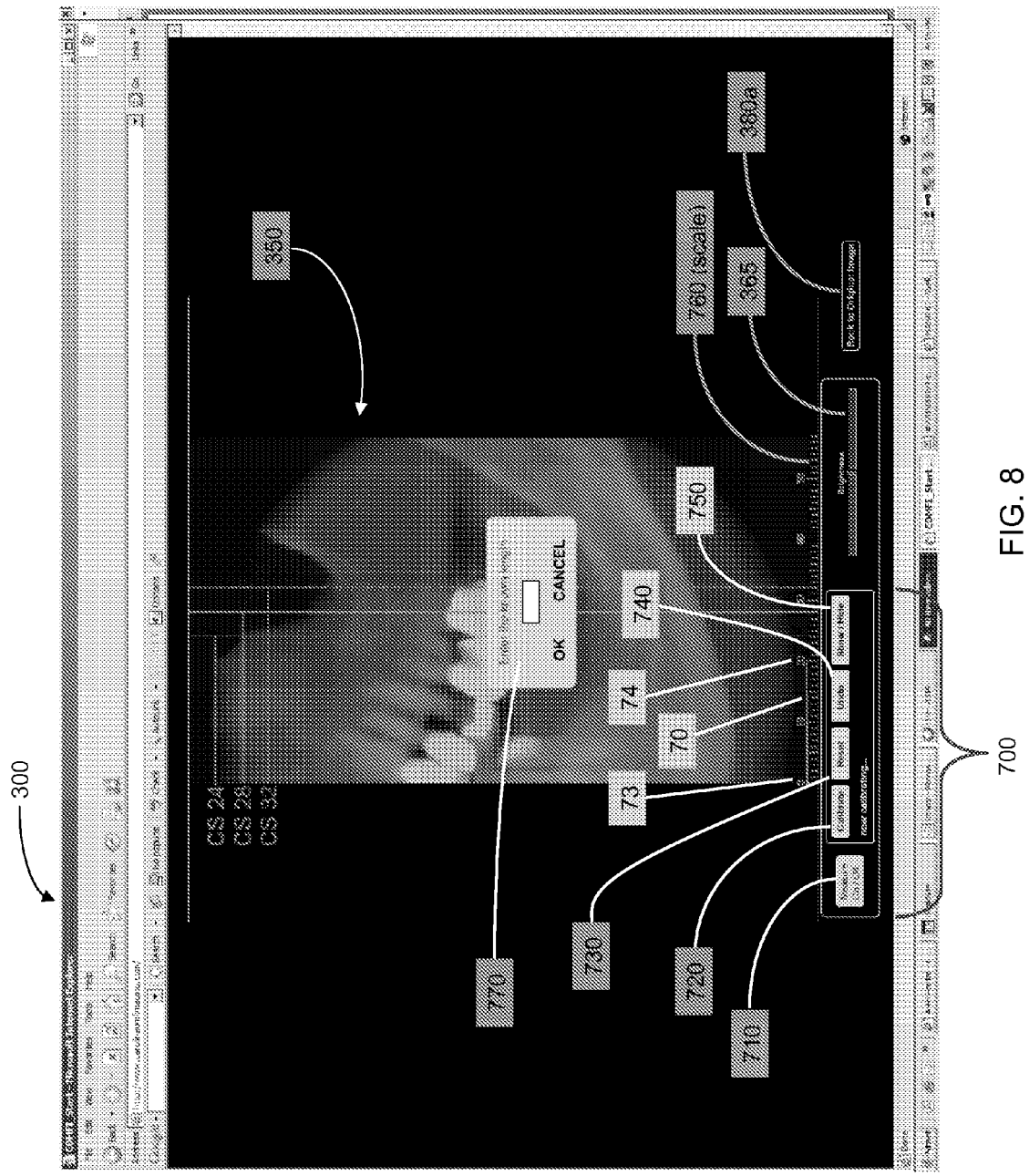

Having thus described the invention in general terms, reference will now be made to the accompanying drawings, which are not necessarily drawn to scale, and wherein:

FIG. 1 schematically illustrates a file architecture or folder system for storing diagnostic imaging data associated with a patient according to one embodiment of the present invention;

FIG. 2 schematically illustrates a template for a multimedia presentation of a composite diagnostic file having patient imaging data combined with diagnostic data, according to one embodiment of the present invention;

FIG. 3 schematically illustrates a populated multimedia presentation of a composite diagnostic file having patient imaging data combined with diagnostic data, according to one embodiment of the present invention;

FIG. 4 schematically illustrates a populated Flash multimedia presentation of a composite diagnostic file having patient imaging data combined with diagnostic data, according to one embodiment of the present invention;

FIG. 5 schematically illustrates a populated Flash multimedia presentation of a composite diagnostic file having patient imaging data combined with diagnostic data, wherein a reference area includes hyperlinks to the patient imaging data, according to one embodiment of the present invention;

FIG. 6 schematically illustrates a populated Flash multimedia presentation of a composite diagnostic file, including an interactive tutorial display for instructing a user on how to access the patient imaging data and the diagnostic data within the composite diagnostic file, according to one embodiment of the present invention;

FIG. 7 schematically illustrates a populated Flash multimedia presentation of a composite diagnostic file having patient imaging data combined with diagnostic data, wherein a larger image area includes measurement functionality allowing a dental provider to establish measurement lines on the larger image, according to one embodiment of the present invention; and FIG. 8 schematically illustrates a populated Flash multimedia presentation of a composite diagnostic file having patient imaging data combined with diagnostic data, wherein a larger image area includes calibration functionality for calibrating the measurement function using a graduated scale displayed in the larger image area, according to one embodiment of the present invention.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

According to embodiments of the present invention, a patient is subjected to a three-dimensional imaging process in a dental imaging center using, for example, a conebeam technology imager or other suitable 3D imaging machine such as, for instance, a Model CB MercuRay for maxillofacial imaging, produced by Hitachi Medical Systems America of Twinsburg, Ohio. Such an imager generally includes a software package, or is otherwise configured to capture a comprehensive set of images of at least a portion of a maxillofacial complex of the patient, otherwise referred to herein as three-dimensional imaging data, in digital form such that the image (s) are storable, executable, or otherwise viewable in two- and three-dimensional form. For example, each image captured by the imaging machine can be saved as a bitmap image (for instance, as a "slice" or image of a two-dimensional aspect of the patient, or as a "three-dimensional volume rendering" or image of a three-dimensional aspect of the patient) in a folder called "bmp" 110 or otherwise saved in a particular file architecture or folder system for each patient under a particular patient identifier. In general, the top level folder can be designated as a "template" 100 until associated with a particular patient. Such a file architecture or folder system is shown, for example, in FIG. 1.

The imaging data obtained from the imager can be stored in the patient-specific folder 100 in different manners. For example, the patient-specific folder may include a media folder 120, a Flash executable file 130, a Flash HTML file 140, and an HTML page in which the Flash HTML file is embedded 150. Within the media folder 120 are two folders called "images" 160 and "video" 170. The "images" folder 160 includes the folder called "bmp" 110 in which the images/volume of data captured by the imaging device are saved. Video clips created from the images/volume of data are, for example, converted to AVI files and stored in the "video" folder 170.

Once the bitmap images from the imaging device have been placed into the "bmp" folder 110 and video clips, if any, placed into the "video" folder 170, any images of interest with respect to the patient condition, including any slice or volume rendering, are sized as necessary, for instance, cropped to 512 by 512 pixels. At the same time, the respective image or video clip may be directly annotated using an appropriate graphics package such as, for example, using Adobe Photoshop. The annotated image, for example, in bitmap form, can then be compressed and saved into a JPEG format in the "images" folder 160. Any annotated video clips are also compressed and converted to Macromedia Flash-type video files using appropriate compression software such as, for example, Sorenson Squeeze.

In order to provide the necessary security for the patient data, such that only the referring dentist or other authorized personnel has access to the data (also for compliance purposes such as, for example, HIPAA regulations), a particular application was created using appropriate software such as ".Net Framework," wherein such an application is otherwise referred to herein as "Referral Works" 200, as illustrated, for example, in FIG. 2. The Referral Works application 200 makes particular use of a standard commercially available multimedia player for delivering the patient data to the referring dentist in a viewable form. Such a multimedia player may comprise, for example, the "Macromedia Flash" application which may be used for files on portable media, such as CD media, as well as online, because the plug-in executable therefor is commonly included on many PC-type computers, the executable is small in file size, and because Macromedia Flash is becoming an increasingly popular Web (Internet) development tool because text and images displayed thereby generally cannot be copied when viewed in a web browser application (i.e., generally causes the text and images to be "read only" in nature).

The Referral Works application 200 includes a "browse" function 210 for locating and opening either the Flash executable file 130 or Flash HTML file 140 that may be located in the appropriate patient folder 100. Upon initiation of the Flash multimedia player, the JPEG images in the "images" folder 160 and any Flash video files in the "video folder" 170 appear under "image" 220 and "video" 230 tabs, respectively, in Referral Works 200. Using appropriate directionality functions, such as the up and down arrows 240, the images and video clips can be highlighted or arranged in any order. When a particular image is selected, a window labeled "Image/Video Description" 250 becomes available for the third party imaging provider or other suitable imaging expert to type a description (diagnosis) or interpretation in text form, with the image being directly associated with such text, for example, with the image being disposed directly adjacent to the text box in the same frame or window. The diagnosis text thus combined with the corresponding image of interest forms a composite diagnostic file (otherwise referred to herein as the "composite file"). In some instances, the composite diagnostic file may include a verbal recording of the diagnosis in addition to or in the alternative to the textual diagnosis. In some embodiments, the textual diagnosis (or a written reference thereto) may include a hyperlink or other electronic pointer associated with a corresponding image of interest (see element 325, of FIG. 5, for example). In other instances, an appropriate video clip from the "video" file may also be included with or in the alternative to the image in the composite diagnostic file.

The Referral Works application 200 further includes functionality for associating the composite diagnostic file with the referring dentist. For example, the Referral Works application can include, for example, a button labeled "Dr" 260 which, when selected, allows the third party imaging provider to place the referring dentist's username, a unique password, and, if necessary, personal information. In addition, the Referral Works application 200 may also implement a button labeled "Pt" 270 to place, for example, the date of treatment for the patient and/or patient personal information with the composite diagnostic file. Further, in a window labeled "Image/Video Reference" 280, a chapter summary of the images and/or video clips can also be created for the particular patient. Once all applicable data has been included in the composite diagnostic file in the Referral Works application, the complete composite diagnostic file is saved by the third party imaging provider at the third party imaging provider site, by the third party imaging provider executing a "File Save" function. To further the security of the patient information, the Referral Works application, when saving the complete composite diagnostic file, creates an encrypted XML file (essentially a "read-only" file) that is placed in the "media" folder, as previously described with respect to the folder architecture.

Opening either the Flash executable file 130 or Flash HTML file 140 in the appropriate patient folder (i.e., clicking on the appropriate link by the referring dentist in a password-protected area for the referring dentist at the online site for the third party imaging provider over the Internet) will open the Macromedia Flash application which, in turn, reads the XML file produced by the Referral Works application. If no XML file is available, a template with blank text and image fields 290 (i.e., fields not populated with information or populated with the word "undefined") is provided as shown in FIG. 3. If an XML file with encrypted data existed, the Macromedia Flash application reads the XML file, and any images and video clips within the "images" folder and "video" folder, respectively, as well as any information typed into any of the text boxes, appears in the resulting Flash multimedia presentation that can be viewed by the referring dentist, as shown generally in FIG. 4.

The Flash multimedia presentation 300 of the composite diagnostic file demonstrates the text fields, and includes a description area 310 and a reference region 320 populated with text. Any images in the XML file appear in a thumbnail region 330, for example, at the bottom of the multimedia presentation 300. When one of the images is selected, the particular selected thumbnail 340 is highlighted in, for example, a different color, and the chosen thumbnail appears as a larger image 350 in a separate field of the multimedia presentation 300. The larger image 350 of the selected thumbnail 340 may be changed in magnification using, for example, provided magnification icons 360a, 360b and/or reset to the original image size by choosing a "RESET" function 370. The larger image 350 of the selected thumbnail 340 can also be caused to populate the entire screen by selecting a "Full Screen Image" function 380. In some embodiments, as shown in FIG. 5, the brightness of the larger image 350 of the selected thumbnail 340 may be adjusted using, for example, a brightness icon 365 (such as a brightness slider bar, for example) that may be provided as a component of the Flash multimedia presentation 300. The brightness icon 365 may also be configured to be present as part of the larger image 350 wherein the larger image 350 populates the entire screen via the "Full Screen Image" function 380 such that a user may adjust the brightness of the larger image 350 in order to highlight various aspects of the image. As shown, for example, in FIG. 5, the reference region 320 may be populated with one or more hyperlinks 325 to one or more images included within the composite diagnostic file such that when the hyperlink 325 (or other electronic "pointer") is selected, the corresponding thumbnail 340 image is highlighted and the selected thumbnail appears as the larger image 350. Thus, a user may use the hyperlinks 325 provided in the reference region 320 to navigate through the various images included within the composite diagnostic file. In some embodiments, the hyperlinks 325 may be included in other regions of the Flash multimedia presentation 300, such as, for example, in the description area 310. Furthermore, the hyperlinks 325 may also be linked to one or more video clips 400 such that the selection of the hyperlink 325 (which may be accessible via the reference region 320) may initiate the playback of the video clip 400. Such flexibility in examining the images and other media designated by the particular thumbnail allows the person viewing the image, such as the referring dentist to see as much detail as necessary or desired.

As shown generally in FIG. 7, the multimedia presentation 300 may further provide a measurement feature that may be used to establish a first point 71 in the larger image 350 and a line 70 extending to a second point 72 in the larger image so as to allow a dental provider to selectively measure a feature (such as an anatomical feature of interest, for example) displayed in the larger two-dimensional image 350. For example, such a measurement feature may allow the dental provider to select a first point 71 in the larger image 350 (by clicking and holding a left mouse button, for example) and drawing a line 70 to a second point 72 in the larger image 350 (wherein the second point 72 may be established by releasing the left mouse button, for example). Such a measurement feature may thus allow a feature to be defined at least in part by the line 70 extending from the first point 71 to the second point 72 in the larger image 350.

The measurement features described herein may also allow the dental provider to selectively display the line 70 extending from the first point 71 to the second point 72 in the larger image 350 and/or a numerical indication 78 of a distance defined between the first point 71 and the second point 72 in the larger image 350. For example, the multimedia presentation 300 may be configured to display a menu 700 of measurement control buttons. The measurement control menu 700 may comprise various control buttons including, but not limited to: a measurement on/off button 710 (which may allow the dental provider to selectively display the remaining measurement function buttons 710, 720, 730, 740, 750); a calibrate button 720 (which may initiate the establishment of a known distance between two calibration points 73, 74 as shown generally in FIG. 8 and as described further herein); a reset button 730 (which may be used to selectively remove the numerical indication 78 established between the first and second points 71, 72 as well as the line 70 described herein); an undo button 740 (which may be used to selectively "undo" the last measurement defined by first and second points 71, 72); and a show/hide button (which may be used to selectively display and/or hide the numerical indication 78 of the distance established by the line 70 in the larger image 350).

In addition, the measurement function described herein (and shown generally in FIGS. 7 and 8), may further comprise a "calibrate" function (initiated, for example via the calibrate button 720 described herein) which may allow a dental provider to establish a known distance between two calibration points 73, 74 located on a graduated scale 760 that may be displayed as part of the larger image 350. For example, by depressing the calibrate button 720 in the measurement menu 700, the dental provider may select a first calibration point 73 on the graduated scale 760 ((by clicking and holding a left mouse button, for example) and drawing a line to a second calibration point 74 on the graduated scale 760 (wherein the second calibration point 74 may be established by releasing the left mouse button, for example). Thus, a known distance on the larger image 350 may be defined at least in part by the line 70 extending from the first calibration point 73 to the second calibration point 74 on the graduated scale 760. Once the dental provider has selected the first and second calibration points 73, 74, the multimedia presentation may then prompt the dental provider to define the known distance by providing at least one calibration input display 770 configured to receive a user-defined numerical value corresponding to the known distance indicated, for example, by the graduations on the graduated scale 760. According to some embodiments, the multimedia presentation 300 may be configured to require the dental provider to complete the calibration process upon activating the measurement function (upon pressing or "clicking" the measurement on/off button 710, for example) to ensure that subsequent measurement lines 70 defined by first and second points 71, 72 selected on the larger image 350 correspond to actual known distances (as defined, for example, by the graduated scale 760).

While the measurement and measurement calibration functions described herein with respect to FIGS. 7 and 8 are shown in the context of a "full screen" multimedia presentation 300 (accessed, for example, by selecting the "Full Screen Image" function 380, as shown in FIG. 4), it should be understood that the multimedia presentation 300 may also allow the dental provider to use the measurement functions described herein in the context of the original larger image 350 display shown generally in FIG. 5. For example, the multimedia presentation 300 may include a "Back to Original Image" function 380a, as shown in FIG. 7, for example. Thus the dental provider may generate the line 70 extending from the first point 71 to the second point 72 in the larger image 350 shown in FIG. 7 and then reduce the larger image 350 to the "original" image size shown in the multimedia presentation 300 view of FIG. 5.

Furthermore, the multimedia presentation 300 may include, for example, checkboxes 390a, 390b, 390c that may be checked or unchecked. Un-checking certain checkboxes may, for example, remove the description and/or reference text areas 310, 320 so as to allow the referring dentist to describe the image(s) to the patient during a patient education session, such that the patient is not distracted by the highly technical medical information in the text areas of the multimedia presentation 300. The checkboxes may also include a checkbox with "Slice Orientation" functionality 390c which, when selected, initiates an animation for demonstrating multi-plane reconstructed slice positions. In addition to the image thumbnail scroll box 330, a video clip scroll box 400 may also be included in the multimedia presentation, where selecting a "Video Clip" functionality will place a video clip in the multimedia presentation in place of the larger image 350. The thumbnail image scroll box 330 can contain, or instance, up to 100 images, and the video clip scroll box 400 can contain, for instance, up to 10 videos.

As shown in FIG. 6, the multimedia presentation 300 may also comprise a tutorial region 600 that may, in some embodiments, be initiated as a Flash presentation upon the opening of the multimedia presentation 300 to provide guidance to a person viewing the multimedia presentation 300 for the first time. The tutorial region 600 may comprise a "close application" function 640 such that a user may choose to close the tutorial region 600. The tutorial region 600 may also include an information region 610 corresponding to one or more tutorial subjects 620 (see also, elements 621, 623, 625, 627) corresponding, for example, to the various features of the multimedia presentation 300. Thus, in some embodiments, the tutorial region 600 may automatically update the information region 610 with text or other descriptive information corresponding to one or more of the tutorial subjects 620 (that may be selected, for example, by a user passing a mouse-controlled pointer over one or more of the tutorial subjects 621, 623, 625, 627. For example, as shown in FIG. 6, if a user selects the "thumbnail images" subject 625, the "thumbnail images" subject 625 may be highlighted in the tutorial region 600 and the information region 610 may be automatically updated to display information corresponding to the "thumbnail images" subject 625. Furthermore, in response to a selection of one of the tutorial subjects 621, 623, 625, 627, the multimedia presentation 300 may also generate one or more tutorial pointers 630 for pointing out regions of the multimedia presentation 300 (such as the thumbnail images 330, 340 and/or video clips 400) corresponding to the selected tutorial subjects 621, 623, 625, 627 (such as the selected "thumbnail images" subject 625 shown generally in FIG. 6).

To produce or otherwise make available the online version of the Flash multimedia presentation 300, a folder with the referring dentist's identification information is placed on a server associated with the third party imaging provider. Such a folder includes an HTML file accessible by the referring dentist through, for example, username and password procedure, though any other suitable controlled access methodology may also be suitable. Information in the HTML file includes, for example, a link to a copy of a particular patient's folder with the same routing, as previously described, including the either the Flash executable file 130 or Flash HTML file 140 in the media folder 120. Also within the media folder 120 is the XML file, the "images" folder 160 (which contains the JPEG images), and the "video" folder 170 (which contains the Flash video files). It thus follows that the XML file can be selectively executed online so as to allow the referring dentist to view the composite diagnostic file of any selected patient of the referring dentist. The online configuration may be configured for many different Web browsers operating on many different platforms (i.e., PC or Macintosh), as necessary, and such an aspect is not considered to be limiting with respect to the scope of the invention.

In addition to, or in the alternative, the composite diagnostic file may be made available to the referring dentist on a portable media element such as, for example, a CD or DVD. Accordingly, to produce the CD/DVD version of the Flash application, all of the contents within the particular patient's folder are included on the CD/DVD for the referring dentist, except the bitmap images within the "bmp" folder 110, the Flash HTML file 140, and the HTML file 150. Finally, an "autostart.inf" file is added to the CD/DVD media such that the Multimedia Flash application automatically executes upon insertion of the CD/DVD into the local dental provider computer device. Due to the encryption of the data included in the XML file, as previously described, individual JPEG images on the CD/DVD may be viewed, but the composite diagnostic file cannot be viewed or edited outside of the automatically-executed Flash application. The portable media element can also be formatted to be viewed in a PC (Windows) or Macintosh environment, or in any other environment found on the local dental provider computer, as necessary, and such an aspect is not considered to be limiting with respect to the scope of the invention.

Thus, embodiments of the present invention provide a solution to delivering images and video clips of patient imaging data in a composite storybook manner, that includes descriptions and/or interpretations directly associated with the images and/or video clips. Such a solution allows the composite diagnostic file to be delivered to the referring dentist on the Web (online) and/or on a portable media element, such as CD/DVD media, with both delivery methods including username and password protection access procedures to allow the application to comply with regulatory requirements such as, for example, HIPAA regulations. The Web version of the application allows the referring dentist to have expedited access to the patient imaging information and associated diagnosis, wherein such access may also be provided to multiple referring dentists, if necessary and properly authorized.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of providing dental-related imaging data of a patient to a dental practitioner, the dental-related imaging data being obtained by a third party imaging provider at a third-party imaging provider site using a three-dimensional digital imaging device, said method comprising:
   obtaining three-dimensional image data of at least a portion of a maxillofacial complex of the patient with the imaging device;
   analyzing the three-dimensional image data so as to form a diagnosis;
   forming a two-dimensional image from the three-dimensional image data, the two-dimensional image being associated with the diagnosis;
   combining the two-dimensional image and the diagnosis to form a composite file, the dental-related imaging data of the patient including the composite file;
   storing the dental-related imaging data at the third-party imaging provider site, in read-only format executable by a standard commercially-available multi-media player;
   making the dental-related imaging data, in encrypted read-only format, available to the dental provider in a secure arrangement, the composite file of the dental-related imaging data thereby being selectively viewable by the dental provider via the multi-media player so as to allow the dental provider to determine an appropriate treatment for the patient, the multimedia presentation comprising a diagnosis display for displaying the diagnosis to the dental provider and an image display for selectively displaying the two-dimensional image associated with the diagnosis to the dental provider;
   allowing the dental provider to selectively measure a feature displayed in the two-dimensional image by selecting a first point in the two-dimensional image and drawing a line to a second point in the two-dimensional image, the feature being defined at least in part by the line extending from the first point to the second point in the two-dimensional image;

displaying a graduated scale in the two dimensional image;

allowing the dental provider to selectively establish a known distance in the two-dimensional image by selecting a first calibration point on the graduated scale and drawing a line to a second calibration point on the graduated scale, the known distance being defined at least in part by the line extending from the first calibration point to the second calibration point on the graduated scale; and allowing the dental provider to define the known distance by providing at least one input display configured to receive a user-defined numerical value corresponding to the known distance.

2. A method according to claim 1 wherein making the dental-related imaging data available to the dental provider in a secure arrangement further comprises making the dental-related imaging data available to the dental provider by publishing the dental-related imaging data on the Internet in encrypted secure read-only format so as to be selectively executable on-line by the dental provider with the standard commercially-available multi-media player.

3. A method according to claim 1 wherein making the dental-related imaging data available to the dental provider in a secure arrangement further comprises making the dental-related imaging data available to the dental provider by saving the dental-related imaging data in encrypted secure read-only format on a portable media element and delivering the portable media element to the dental provider for selective execution of the dental-related imaging data by the dental provider on a local dental provider computer device with the standard commercially-available multi-media player.

4. A method according to claim 1, further comprising allowing the dental provider to selectively display the two-dimensional image associated with the diagnosis on the image display by selecting at least one executable link from the diagnosis display, the two-dimensional image being associated with the at least one executable link such that the two-dimensional image is accessible to the dental provider from the diagnosis display.

5. A method according to claim 1, wherein making the dental-related imaging data available to the dental provider in a secure arrangement further comprises displaying the composite file to the dental provider in a multimedia presentation, the multimedia presentation comprising a tutorial display for directing the dental provider to the diagnosis and the two-dimensional image associated therewith.

6. A method according to claim 1, wherein allowing the dental provider to selectively measure a feature displayed in the two-dimensional image further comprises:

allowing the dental provider to selectively display a numerical indication of a distance defined between the first point and the second point in the two-dimensional image; and allowing the dental provider to selectively display the line extending from the first point to the second point in the two-dimensional image.

* * * * *